(12) United States Patent
Sasaki et al.

(10) Patent No.: US 6,764,654 B2
(45) Date of Patent: Jul. 20, 2004

(54) FLAT CELL AND AN ANALYZER USING THE SAME

(75) Inventors: Hiroshi Sasaki, Mito (JP); Yutaka Ito, Takahagi (JP); Katsuhiro Kambara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/101,424

(22) Filed: Mar. 20, 2002

(65) Prior Publication Data

US 2003/0064005 A1 Apr. 3, 2003

(30) Foreign Application Priority Data

Sep. 25, 2001 (JP) .......................................... 2001-290531

(51) Int. Cl.⁷ ................................................. B01I 3/00
(52) U.S. Cl. ......................................... 422/102; 356/244
(58) Field of Search ......................... 422/102; 356/244, 356/245, 246

(56) References Cited

U.S. PATENT DOCUMENTS

| | | | | |
|---|---|---|---|---|
| 5,041,266 A | * | 8/1991 | Fox | ............................ 422/102 |
| 5,200,152 A | * | 4/1993 | Brown | ........................ 422/102 |
| 5,831,184 A | * | 11/1998 | Willard et al. | ............ 73/864.91 |
| 6,287,872 B1 | * | 9/2001 | Schurenberg et al. | ........ 436/181 |
| 6,479,157 B1 | * | 11/2002 | Yoneda et al. | .............. 428/429 |
| 6,500,553 B1 | * | 12/2002 | Yoneda et al. | .............. 428/448 |
| 6,555,813 B1 | * | 4/2003 | Beecher et al. | ............. 250/281 |

FOREIGN PATENT DOCUMENTS

| JP | 11-14617 | 1/1999 |
|---|---|---|
| JP | 11-311168 | 11/1999 |

* cited by examiner

Primary Examiner—Jeffrey R. Snay
(74) Attorney, Agent, or Firm—McDermott Will & Emery LLP

(57) ABSTRACT

A measurement cell for analyzer for carrying out qualitative and/or quantitative analysis for one or more substances by an optical means, which is planar and has sample-holding portions, the contact angle between said sample-holding portion and water being 30° or less, and the contact angle between the other portion of said plane and water being 100° or more, permits a plurality of measurements with a single cell for the same one sample, repeated use and reduction of the amount of sample than before.

6 Claims, 5 Drawing Sheets

ADHESION OF SAMPLES

ADDITION OF VARIOUS INDICATORS

ADHESION OF SAMPLES

ADDITION OF VARIOUS INDICATORS

WHEN TRANSMITTANCE OR ABSORBANCE IS MEASURED

WHEN REFLECTANCE IS MEASURED (1) WHEN TRANSMITTANCE OR ABSORBANCE IS MEASURED (2) WHEN REFLECTANCE IS MEASURED

HYDROPHILIC PATTERN OF A
FLAT CELL AFTER ADHESION
OF A SAMPLE TO THE
PATTERN AND ITS DRYING

FLAT CELL AND AN ANALYZER USING THE SAME

The present invention relates to a measurement cell for analyzer for qualitative and/or quantitative analysis for substances contained in blood, urine, water or the like, and an analyzer using the cell.

PRIOR ART

In an analyzer for qualitative and/or quantitative analysis for a small amount of elements contained in blood, urine, water (e.g., drinking water and river water) or the like, a liquid sample is usually placed in a rectangular parallelepipedic cell and subjected to qualitative and/or quantitative analysis by measuring an optical property such as absorbance, transmittance, reflectance, fluorescence intensity or the like. Even when one sample is analyzed, the measurement of two or more items requires samples for measurement in the same number as that of the items. For example, in the case of urine, sugars, proteins, pH, ketone bodies, blood, urobilinogen, bilirubin, amylase and the like are measured. In the case of blood, cholesterol, cholinesterase, phosphatase, GOT, GPT and the like are measured. In the case of water, pH, contained elements (e.g., ions of metals such as sodium, cadmium, lead etc., chlorine ions and cyano ions), turbidity and the like are measured. Although there are very few methods each for carrying out qualitative and/or quantitative analysis for two or more substances among the above-exemplified substances, one analysis method is adopted for qualitative and/or quantitative analysis for each substance in most cases. Therefore, cells in the same number as that of measurement items are necessary even when one sample is analyzed. For example, in the case of blood, there are about 60 measurement items.

In the case of a blood analyzer, the miniaturization of a cell is in progress in order to reduce the amount of a sample for analysis as much as possible for the purpose of reducing a burden on a human being who takes an examination. However, when the cell is miniaturized, the sample becomes difficult to place in the cell. Even if the sample can be placed in the cell, bubbles remain in the cell, so that exact measurement by absorbance, transmittance and the like cannot be made. This problem is remarkable when the surface tension of the sample is high. In addition, the cell once used is washed and a liquid used for the washing is removed from the cell by suction or drying, after which the cell is reused for the measurement. Therefore, the cell requires a washing step. Since the cell is often a rectangular parallelepiped, the position of a nozzle for water jet is required to be accurate for certain introduction of water for washing into the cell in order to wash the interior of the cell. Moreover, for the same reason as above, the exhaust of a liquid sample and the injection and exhaust of a washing liquid become difficult also in the washing of the cell with a decrease of the size of the cell. That is, also in this regard, the miniaturization of the cell is limited. The bubbles can be removed in some cases by vibrating the cell with an ultrasonic washer or the like, but the cell should be vibrated also in washing of the cell in order to fill the cell with water for washing. Therefore, a large-scaled apparatus is necessary.

As a method for reducing the amount of a sample which is required for the measurement, there is also a method of increasing the volume of the sample by diluting the sample with water. However, if the sample is diluted with water, the resulting sample has a high surface tension and hence is more difficult to place in a small cell, as described above. In addition, the ratio of the absorbance of the sample to that of a reference is decreased by the dilution, resulting in a low precision of measurement. For the dilution, an alcoholic organic solvent is used in some cases in place of water but is disadvantageous in that there are samples hardly soluble in solvents other than water or that the absorption spectrum of the resulting dilution is changed by the addition of an indicator. As described above, the reduction of the amount of a sample is difficult in a measuring method using a present-day rectangular parallelepipedic cell.

As a prior art, there is "Test Piece for Liquid Sample and Process for Production Thereof" (JP-A-11-14617). This test piece has a structure in which sample-holding portions comprising a water-soluble polymer and an indicator are provided on the surface of a polystyrene plate, and it permits measurement using a sample in an amount smaller than that required in the case of a rectangular parallelepipedic cell. The test piece, however, cannot be reused after washing unlike an ordinary measurement cell because the indicator has been previously held in the sample-holding portion. The reason is that the test piece invented is similar to pH test paper and the like.

As described above, when items measured for even one sample are increased, the number of cells used is increased, so that a necessary number of cells should be prepared. Moreover, cells in a number necessary for the measurement items should be washed after the measurement.

The amount of a sample cannot be reduced merely by miniaturizing a measurement cell having a conventional structure or by diluting the sample.

There has been a desire for a cell and a measuring apparatus which make it possible to measure two or more items for one sample and make the amount of the sample smaller than that required at present. The cell should be repeatedly used by operations such as washing.

SUMMARY OF THE INVENTION

We investigated in order to solve the above problems, and consequently found that the following flat plate functions as a cell capable of solving the above problems (hereinafter referred to as "flat cell"): a flat plate which is made of a material capable of transmitting or reflecting measuring light and has a water-repellent surface formed thereon and having a plurality of hydrophilic patterns. On the basis of this finding, the present invention has been accomplished.

The details of means for solving the above problems are described below.

(1) A measurement cell for analyzer for carrying out qualitative and/or quantitative analysis for one or more substances by an optical means, which has the following characteristics: a sample to be subjected to measurement is liquid; the shape of said measurement cell is substantially planar; the cell has sample-holding portions in said plane; the contact angle between the sample-holding portion and water is 30° or less; the contact angle between the other portion of said plane and water is 100° or more; and said measurement cell can be repeatedly used by washing and drying.

(2) The measurement cell for analyzer according to the above item (1), characterized in that a layer of a compound having any of the following structures is formed on the portion other than the sample-holding portions:

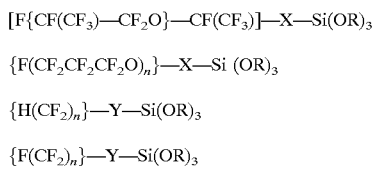

wherein X is a linking site between a perfluoro polyether chain and an alkoxysilane residue, Y is a linking site between a perfluoroalkyl chain and an alkoxysilane residue, and R is an alkyl group.

(3) An analyzer for qualitative and/or quantitative analysis for one or more substances by an optical means, which has the following characteristics: a sample to be subjected to measurement is liquid; the shape of cells used for the measurement is substantially planar; each of the cells has sample-holding portions in said plane; the contact angle between the sample-holding portion and water is 30° or less; the contact angle between the other portion of said plane and water is 100° or more; said measurement cells can be repeatedly used by washing and drying; and the analyzer has therein at least a conveying mechanism for said cells, a sample sticking mechanism, an indicator sticking mechanism and an optical measurement mechanism.

(4) The analyzer according to the above item (3), characterized in that a layer of a compound having any of the following structures is formed on the portion of said cell which is other than the sample-holding portions:

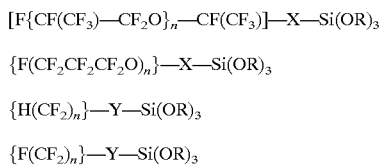

wherein X is a linking site between a perfluoro polyether chain and an alkoxysilane residue, Y is a linking site between a perfluoroalkyl chain and an alkoxysilane residue, and R is an alkyl group.

(5) A cell for subjecting a sample to measurement which has two or more hydrophilic patterns having a contact angle with water of 30° or less and a water-repellent portion having a contact angle with water of 100° or more, and is planar.

(6) The cell according to the above item (5), which transmits 60% or more of light having a wavelength of 340 to 800 nm which is incident upon the cell.

(7) The cell according to the above item (5), which transmits 80% or more of light having a wavelength of 400 to 800 nm which is incident upon the cell.

(8) The cell according to the above item (5), wherein a plate for the cell is a metal that reflects light.

(9) The cell according to the above item (5), wherein the surface roughness of the sample sticking area is Ra 100 nm or less.

Other objects, features and advantages of the invention will become apparent from the following description of the embodiments of the invention taken in conjunction with the accompanying drawings.

(1) When transmittance or absorbance is measured.

(2) When reflectance is measured.

Figure 4:
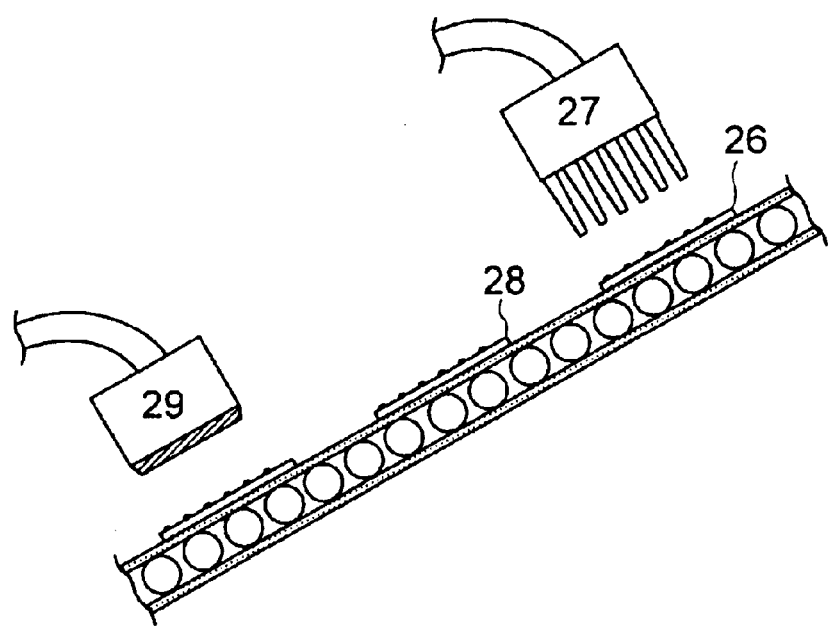

FIG. 4 illustrates the flat cell washing mechanism of the analyzer of the present invention.

Figure 5:
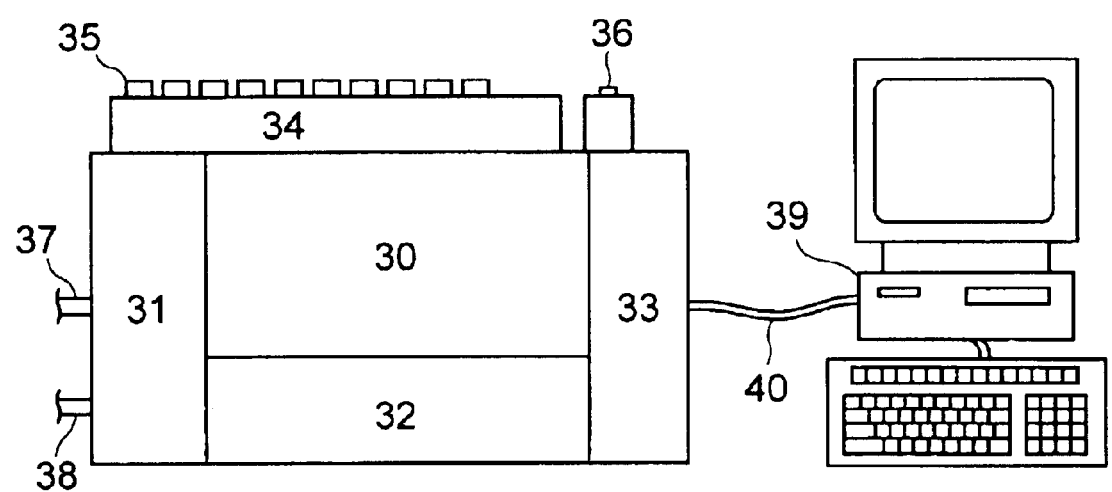

FIG. 5 illustrates the structure of the analyzer of the present invention.

Figure 6:
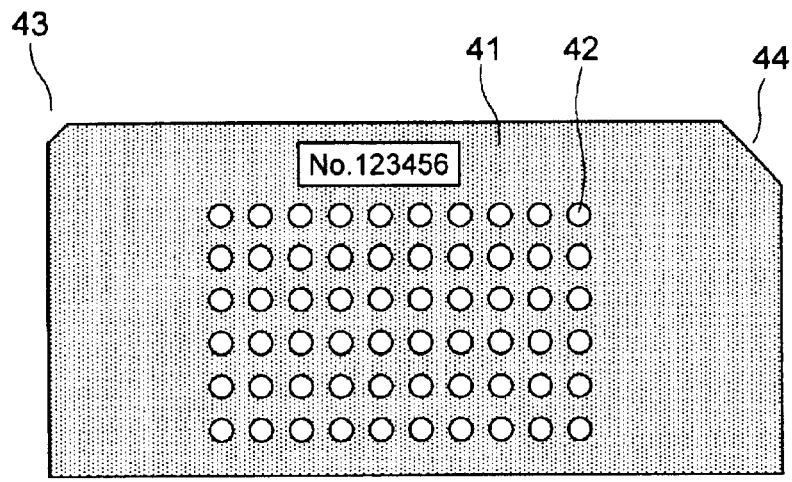

FIG. 6 shows a flat cell produced and used in Example 1.

Figure 7:
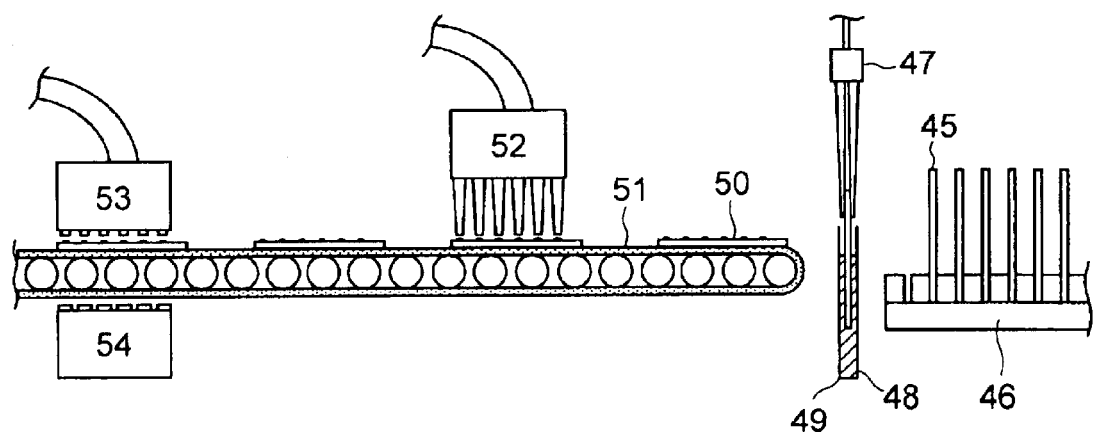

FIG. 7 shows the measuring mechanism of an analyzer used in Example 2.

Figure 8:
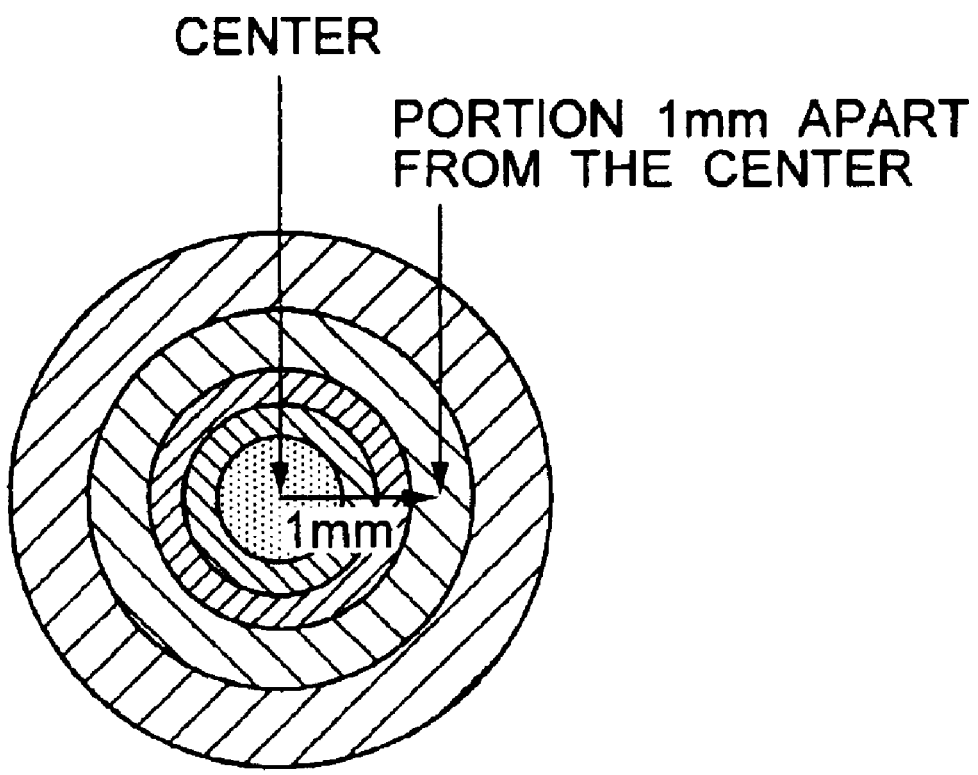

FIG. 8 shows transmittance-measuring portions in a hydrophilic pattern.

The meanings of the reference numerals in the above figures are as follows.

1 and 41—water-repellent portions, 2—hydrophilic pattern, 3, 17 and 49—liquid samples, 4 and 5—pipets, 6—an analyzing reagent, 7 and 11—light sources, 8 and 12—measuring lights, 9—light not absorbed by a sample and a flat cell, 10, 14, 20, 25 and 54—light receptors, 13—light which has been reflected on the surface of a cell and has re-passed through a droplet on a hydrophilic pattern, 15—dispenser, 16, 26 and 45—flat cells, 18—dispenser for indicator delivery, 19, 24 and 53—light exposure units, 21 and 51—belt conveyors, 22—belt conveyor driving roll, 23—optical system, 27—washer, 28—washed flat cell, 29—dryer, 30—measuring mechanism, 31—flat cell washing mechanism, 32—mechanism for conveying a washed flat cell, 33—flat cell accommodating mechanism, 34—mechanism for storage and supply of analyzing reagents, 35—feed opening for indicator, 36—feed opening for liquid sample, 37—piping for water supply, 38—piping for drainage, 39—control unit, 40—cable, 42—hydrophilic pattern, 43 and 44—cut portions for positioning a flat cell, 46—flat cell cartridge, 47—tweezers, 48—vessel for liquid sample, 50—flat cell having a liquid sample adhering thereto, 52—dispenser for indicator delivery.

DETAILED DESCRIPTION OF THE INVENTION

Unlike conventional three-dimensional cells, the measurement cell of the present invention is planar and hence can easily be produced. Moreover, its production cost is lower than that of the three-dimensional cells. The measurement cell of the present invention requires only a smaller amount of a sample and can be reused after washing and drying. The washing and drying are easy because said cell is planar.

As the sample, any sample can be subjected to measurement so long as it is liquid or can be liquefied by dissolution or suspension in a solvent.

Embodiments of the present invention are explained below.

[1] Abridged Description of the Flat Cell of the Present Invention and Measuring Methods According to the Present Invention.

Figure 1:
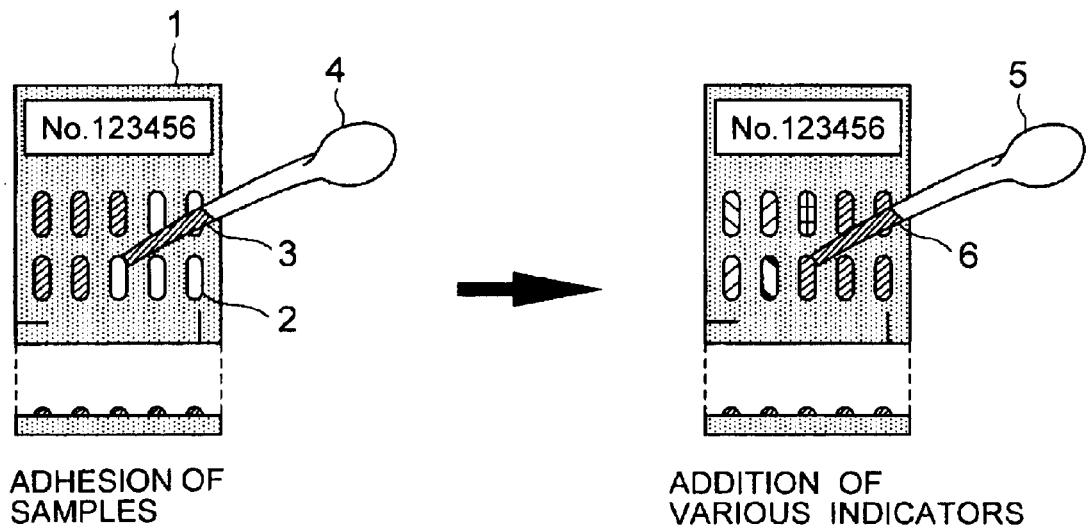
FIG. 1 illustrates the structure of the flat cell of the present invention and a method for applying a liquid sample and adding indicators.

The structure of the flat cell of the present invention and a method for applying a liquid sample and adding indicators are explained with reference to FIG. 1.

The flat cell is a flat plate having a water-repellent surface formed thereon and having a plurality of hydrophilic patterns 2. The hydrophilic patterns are sample-holding portions and the other portion is a water-repellent portion.

In the present specification, a plane or a substantial plane refers to a surface having such a roughness that in carrying out the optical measurement described hereinafter, scattering of transmitted or reflected light is negligible as compared with the precision of measurement. A plate having such a plane is referred to as a flat plate. An example of specific numerical value is as follows: the roughness is about Ra 100 nm or less which is approximately one-fourth the wavelength of measuring light. The following interpretation is made: providing a projection or the like in a portion other than portions used for the measurement (e.g., the side portion of the cell which is not used for the measurement) does not hinder the above-mentioned presence of a plane.

The portion other than the hydrophilic patterns is water-repellent. In the present invention, a conventional rectangular parallelepipedic cell corresponds to each hydrophilic pattern. When a liquid sample 3 is dropped on a portion of the cell in which the hydrophilic pattern is present or near this portion with a pipet 4 or the like, the liquid sample adheres only to the hydrophilic pattern portion.

Then, an indicator 6 is applied on the portion having the liquid sample adhering thereto, with a pipet 5. An analyzing reagent of each kind is applied on the corresponding hydrophilic pattern. In the case shown in FIG. 1, 10 hydrophilic patterns are present in the flat cell, so that 10 kinds of measurements can be carried out by the use of one liquid sample. When the cell is allowed to stand in such a state for several minutes, the droplet on the hydrophilic pattern is concentrated by the evaporation of a solvent to be flattened.

Figure 2:
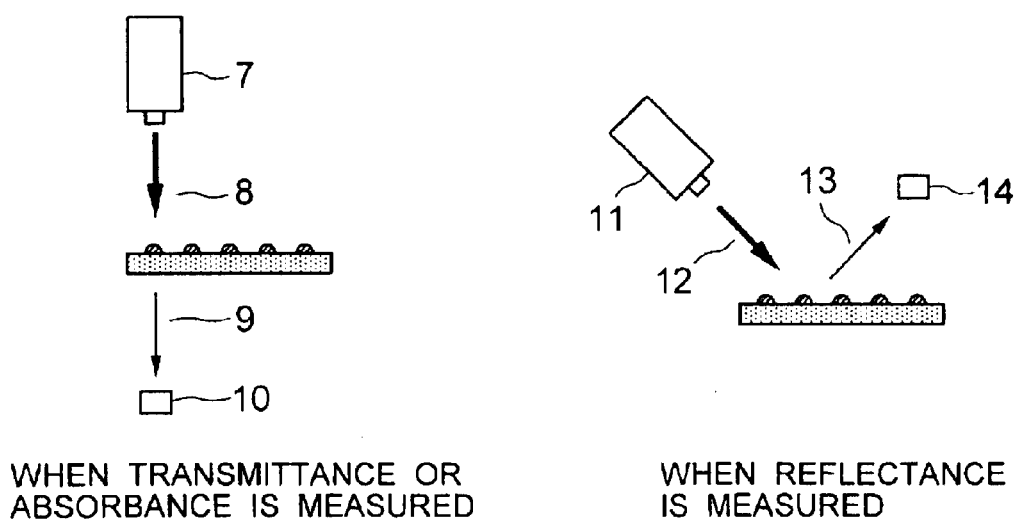
FIG. 2 illustrates measuring methods using the flat cell of the present invention.

Next, the measuring methods are described below with reference to FIG. 2.

When a plate for the flat cell transmits measuring light to a certain extent, measurement is carried out by the use of the transmittance or the absorbance calculated on the basis of the transmittance. Specifically, measuring light 8 emitted by a light source 7 passes through the droplet on the hydrophilic pattern and the plate and a portion thereof is absorbed by them. The unabsorbed light 9 reaches a light receptor 10. A specific component in the sample is quantitated from the attenuation factor of the measuring light at a measuring wavelength. When a plate for the flat cell reflects measuring light to a certain extent, measurement is carried out by the use of the reflectance. Specifically, measuring light 12 emitted by a light source 11 passes through the droplet on the hydrophilic pattern, is reflected from the cell surface again, and passes through the droplet on the hydrophilic pattern again. In this process, a portion of the measuring light is absorbed by the droplet and the cell surface. The unabsorbed light, i.e., light 13 that has been reflected from the cell surface and has again passed through the droplet on the hydrophilic pattern reaches a light receptor 14. A specific component in the sample is quantitated from the attenuation factor of the measuring light at a measuring wavelength.

In the above measuring methods, the contact angle between the sample-holding portion and water should be 30° or less, and the contact angle between the other portion of the plane and water should be 100° or more. The reason is that when this contact angle is less than 100°, the sample adheres to the portion other than the hydrophilic patterns, so that a bridge-like droplet is liable to be formed among two or more of the patterns. Particularly when measurements are carried out for a plurality of different items, erroneous results tends to be obtained owing to mixing of liquids. This fact is described in detail in the examples described hereinafter.

The measurement using the absorbance or the transmittance is effective in subjecting a turbid liquid sample to the measurement or measuring the turbidity. The measurement using the reflectance is effective for a liquid sample having a low concentration, because measuring light goes to and from the cell surface in the droplet. However, when a turbid liquid sample that tends to increase the proportion of scattered light is subjected to this measurement, the measured values are inaccurate in some cases. It should be noted that the measured values are liable to be affected by fine concavities and convexities on the cell surface.

[2] Production Process of the Flat Cell

Various production processes of the flat cell are thought of, though of these processes, the following two processes (1) and (2) are explained herein.

(1) Impartment of Water-Repellency After Masking of Hydrophilic Pattern Portions The flat cell is produced by the following steps (i) to (iv). The step (i), however, may be omitted when it is unnecessary.

(i) Impartment of Hydrophilicity

When the contact angle between a plate for the cell and water is large, the surface of the plate is made hydrophilic. When a plate for the cell has a high hydrophilicity, its surface need not be made hydrophilic.

A method for the impartment of hydrophilicity is varied depending on a plate for the cell. Specifically, the following methods can be exemplified.

1) Methods Adopted When the Plate is a Metal

When the plate for the cell is a metal, the contact angle between the plate and water is often 70° or more. When the plate is aluminum, the contact angle between the plate and water is approximately 90 to 95°. When the plate is stainless steel, the contact angle between the plate and water is approximately 70 to 95° though depending on the kind of stainless steel. When such a plate is made hydrophilic, the contact angle can be reduced by dip in hydrochloric acid, nitric acid, sulfuric acid or the like. When the plate is aluminum, the contact angle is reduced to approximately 10 to 20° by dip in a mixture of 30 wt % nitric acid and 5 wt % hydrochloric acid for approximately 5 to 10 minutes. Also when the plate is stainless steel such as SUS304, 316 or the like, the contact angle is reduced to approximately 10 to 20° by dip in 30 wt % nitric acid for approximately 5 to 10 minutes. In addition, when the plate is Fe-42Ni, the contact angle is reduced to 10° or less by dip in 15 wt % nitric acid for approximately 1 to 2 minutes.

As another method, a treating method using $O_2$ plasma can be exemplified. When the plate is aluminum or stainless steel, the contact angle between the plate and water is 20° or less under the following conditions: oxygen partial pressure 1 Torr, output of high-frequency power source 300 W, and treatment time 3 minutes.

2) Methods Adopted When the Plate is Glass or Quartz

When the plate is glass or quartz, its hydrophilicity can be improved, for example, by treatment with $O_2$ plasma or dip in a basic solution. In the case of the treatment with $O_2$ plasma, the contact angle between the plate and water becomes 100 or less under the following conditions: oxygen partial pressure 1 Torr, output of high-frequency power source 300 W, and treatment time 3 minutes. In the case of the dip in a basic solution, the contact angle between the plate and water becomes 20° or less after dip in a 1 wt % aqueous sodium hydroxide solution.

3) Methods Adopted When the Plate is a Resin

When the plate is a resin, its hydrophilicity can be improved, for example, by treatment with $O_2$ plasma or dip in an acidic or basic solution.

In the case of the treatment with $O_2$ plasma, when the plate is, for example, a polystyrene, acrylic resin, styrene-acrylic resin, polyester resin, acetal resin, polycarbonate, polysulfone or polyether sulfone, the contact angle between the plate and water becomes 200 or less under the following conditions: oxygen partial pressure 1 Torr, output of high-frequency power source 100 W, and treatment time 1 minute.

The dip in a basic solution is especially effective when there is used a material having ester bonds in the molecule, such as an acrylic resin, styrene/acrylic resin, polyester resin, acetal resin, polycarbonate or the like. The reason is that the severance of ester bonds present in or near the surface of the material produces highly hydrophilic carboxylate residues and/or hydroxyl groups to improve the hydrophilicity of the surface in general. Even when there is used a resin that is produced by polymerization caused by the condensation of an amino group with a carboxyl group, such as a polyimide, a polyamide or the like, the hydrophilicity of the surface of the resin can be generally improved either by making amino groups remained unreacted after the polymerization into a highly hydrophilic ammonium salt structure by dip in an acid such as hydrochloric acid, or by making carboxylic groups remained unreacted after the polymerization into a highly hydrophilic carboxylate by dip in an aqueous sodium hydroxide solution. In the dip in the acidic or basic solution, the impartment of hydrophilicity tends to proceed more rapidly with a rise of the temperature of the solution and an increase of the concentration of the solution. Thus, although the dip is useful, care should be taken in carrying out the dip because increasing the temperature and/or the concentration tend to damage the plate in some cases.

4) Methods Applicable to Various Plates

As methods which permit impartment of hydrophilicity whichever material may be selected from metals, glass and resins as the plate, there can be exemplified a method comprising application of a coating material capable of exhibiting hydrophilicity, ultraviolet irradiation, and a method comprising allowing the plate to stand under an ozone atmosphere. The details of the method comprising application of a coating material capable of exhibiting hydrophilicity are described in the section of "Hydrophilic materials, coating materials and a treating method".

(ii) Formation of a Mask

Portions where hydrophilic patterns are to be formed are masked (protected) because the pattern portions made hydrophilic should be left after the impartment of water-repellency described hereinafter. For the masking, a printing method is suitable because it permits easy assurance of the accuracy of positions. As the printing method, there can be exemplified a method of placing a cell in a printer, an ink-jet printer or the like in place of printing paper and printing a masking material on the cell, and a so-called screen printing, i.e., a method of previously forming a mask having holes in portions corresponding to hydrophilic patterns, placing the mask on a plate for cell, and rubbing a roller having a masking material (e.g., ink) adhered thereto, against the mask. The masking material is explained hereinafter. As the masking material, a material easily removable by dissolution in water or an organic solvent is suitable because the masking material should be removed after the impartment of water-repellency. For example, as a water-soluble masking material, water-soluble ink, aqueous solutions of water-soluble polymers and the like are suitable. The water-soluble polymers are useful also in being liable to repel a water-repellent material as described hereinafter. As a masking material soluble in an organic solvent, ink for offset printing, a toner for laser printer, and the like are suitable. As an apparatus for forming the mask, an office or domestic ink-jet printer using water-soluble ink is suitable because it uses the easily water-soluble ink and has a high precision of discharging position. Masking with a tape or a seal is also effective as another method. As a material for the adhesive portion of the tape or seal, there is preferably used a water-soluble polymer specific examples of which are poly(vinyl alcohol)s and poly(acrylic acid)s.

(iii) Water Repellent Treatment

Water-repellency is imparted to the plate surface. As an agent for this treatment, there are, for example, treating agents to be merely applied, and treating agents to be fixed on the surface by heat treatment or light irradiation. The treating agents to be fixed on the surface are more suitable because they can keep the stability of shape of the hydrophilic patterns high when the cell is repeatedly used. If a water-repellent material is not fixed, it flows into the hydrophilic pattern portions to cover their surfaces in some cases owing to washing operation and the like when the cell is repeatedly used. The treating agents to be fixed on the surface by heat treatment after application on the surface are described hereinafter.

(iv) Mask Removal

The mask formed above is removed. As a method for removing the mask, there are operations such as washing with a solvent, peeling of the masking material by the use of an adhesive tape, etc.

(2) Formation of Hydrophilic Patterns After the Impartment of Water-Repellency

In this process, hydrophilic patterns are formed after subjecting a plate for the cell previously to the above-mentioned treatment for imparting water-repellency. As a method for forming the hydrophilic patterns, there can be exemplified a method of decomposing and removing a material for the impartment of water-repellency by irradiating the surface having water-repellency imparted, with laser beams, electron beams or ultraviolet rays, and a method of decomposing the material for the impartment of water-repellency by bringing a flatiron at a high temperature into contact with portions where the hydrophilic patterns are to be formed. Even when a material having a high water-repellency by nature is used as a plate for the cell, mixing of aliquots of a liquid sample in the hydrophilic patterns is likely to be caused which is described hereinafter, if the contact angle between the plate and water is less than 100°. In order to prevent the mixing, the impartment of water-repellency is necessary.

[3] Plate for the Cell

As a plate for the cell, either a material capable of transmitting measuring light or a material capable of reflecting measuring light is chosen. For example, in the case of a medical analyzer for blood, urine and the like, the wavelength of measuring light is usually 340 to 800 nm, so that it is preferable to use a plate capable of transmitting or reflecting light with such a wavelength to a certain extent. In the present specification, the expression "to a certain degree" means such a degree that 60% or more of light having a wavelength of 340 to 800 nm which is incident upon the plate is transmitted and that 80% or more of light having a wavelength of 400 to 800 nm which is incident upon the plate is transmitted. The quantitativeness in the measurement increases with an increase of the evenness of the plate. This is because the proportion of irregular reflection of measuring light increases when the evenness is low.

(1) Material Capable of Transmitting Measuring Light

The material capable of transmitting measuring light includes glass, transparent resins, etc. For improving the quantitativeness, a material having high transmitting properties for measuring light is preferable. Resins having high transmitting properties for measuring light include polystyrenes, acrylic resins, styrene/acrylic resins, polyester resins, acetal resins, polycarbonates, polyether sulfones, polysulfones, etc. The reason is that a 0.1-nm thick plate of any of these resins is suitable for the measurement because it transmits 60% or more of light having a wavelength of 340 to 800 nm which is incident upon the plate and it transmits 80% or more of light having a wavelength of 400 to 800 nm which is incident upon the plate. With a decrease of the thickness of the plate, the transmittance increases, so that the quantitativeness increases. However, if the plate is too thin, problems such as bending are caused when the cell is held or a sample adheres to the cell. Therefore, in view of the strength of the plate, the plate should have such a thickness that the plate is easy to handle.

When there is used a material that is subjected to heat treatment in the impartment of water-repellency described hereinafter, the material should have heat resistance.

(2) Material Capable of Reflecting Measuring Light

As the material capable of reflecting measuring light, metal plates subjected to mirror polishing can be exemplified. As materials for the metal plates, aluminum, iron-nickel alloys, stainless steels, etc. can be exemplified. Materials obtained by vapor deposition of aluminum or the like on a glass plate can also be exemplified. As the iron-nickel alloys, those having a low iron content are hardly corroded and hence are characterized in that the cell can be used over a long period of time. The stainless steels are advantageous in their low corrosiveness. Specific examples of the stainless steels are SUS201, SUS202, SUS301, SUS302, SUS303, SUS303SE, SUS304, SUS304L, SUS304N1, SUS304N2, SUS304LN, SUS305, SUS309S, SUS310S, SUS316, SUS316L, SUS316N, SUS316LN, SUS316J1, SUS316J1L, SUS317, SUS317L, SUS317J1, SUS321, SUS347, SUSXM7, SUSXM15J1, SUS329J1, SUS405, SUS410L, SUS430, SUS430F, SUS434, SUS447J1, SUSXM27, SUS403, SUS410, SUS410J1, SUS416, SUS420J1, SUS420F, SUS431, SUS440A, SUS440B, SUS440C, SUS440F, SUS630, SUS631 etc.

[4] Hydrophilic Material, a Coating Material and a Treating Method

There are described below hydrophilic coating materials (coating materials capable of exhibiting hydrophilicity) used for impartment of hydrophilicity which is applicable to the above-exemplified various plates. In the following description, a step of applying a coating material includes after-treatments such as heating and drying.

As the coating materials, those described in the following items (1) to (4) can be exemplified in general. Needless to say, other coating materials may be used without any limitation so long as they have the effects described below.

(1) Solutions of Water-Soluble Polymeric Materials

As the water-soluble polymer, there can be exemplified polyethylene glycols, poly(vinyl alcohol)s, poly(acrylic acid)s, polyacrylates, poly(allylamine)s, poly(allylammonium chloride)s, starch, etc. When the chemical structures of these polymers are noted, there can be exemplified water-soluble polymers having hydrophilic groups (e.g., hydroxyl group, amino group, carboxyl group and salt structure groups) in the molecule. An aqueous solution of any of these polymers or a solution of any of these polymers in an organic solvent is prepared as a coating material, applied on a plate for the cell and then dried to form a hydrophilic coating film. Of the above-exemplified water-soluble polymers, the polyethylene glycols, in particular, have a strong tendency to reduce the contact angle of the surface coated with the coating material. The molecular weight of the polymer used is preferably as high as possible because when the molecular weight is higher, a smoother hydrophilic film can be formed which causes slighter light scattering. When the surface to be treated has a high water-repellency by nature, it repels the coating material, so that an even film cannot be formed in some cases. Particularly when a solvent used in the polymer solution is water, the surface tension of the solution is high, so that the formation of an even film is apt to be impossible. Previous treatment of the surface with $O_2$ plasma before the application of such a coating material on the surface is effective because it facilitates the formation of an even coating film. A polyethylene glycol is soluble also in an organic solvent such as tetrahydrofuran. A solution of a polyethylene glycol in an organic solvent has a lower surface tension than does an aqueous solution of the polyethylene glycol and hence can easily be applied on the surface of aluminum or the like, which has a high water-repellency.

(2) Coating Materials Containing Hydrophilic Particles

A mixture of an alkoxysilane solution and a dispersion containing hydrophilic alumina particles or hydrophilic silica particles can be used as the coating material. When this coating material is used, the formation of a film is completed by heating a plate for the cell after the application of the coating material. In this coating material, the hydrophilic alumina particles or hydrophilic silica particles exhibit hydrophilicity mainly, and the alkoxysilane functions mainly as a support for the particles. Therefore, the hydrophilicity of the coating material can be enhanced by increasing the proportion of the hydrophilic alumina particles or hydrophilic silica particles. Increasing the proportion of the alkoxysilane improves the physical strength of the film. The alkoxysilane preferably involves a certain degree of intermolecular crosslinking because the proportion of the alkoxysilane evaporated by heating after the application of the coating material is reduced. Hydrochloric acid or the like is added to the alkoxysilane in some cases in order to accelerate intermolecular polymerization. On the other hand, the dispersion of hydrophilic silica is basic in some cases in order to improve the dispersibility of silica. Therefore, when the alkoxysilane solution and the hydrophilic-silica dispersion are mixed, hydrophilic silica is aggregated in some cases. Accordingly, due attention should be given to the liquidness of the mixture and the dispersed state of hydrophilic silica in the mixture. In this respect, hydrophilic alumina hardly causes a trouble because its dispersion is mainly acidic. The alkoxysilane includes methyltrimethoxysilane, ethyltrimethoxysilane, butyltrimethoxysilane, methyltriethoxysilane, ethyltriethoxysilane, butyltriethoxysilane, tetramethoxysilane, tetraethoxysilane, etc. An alkoxytitanium may be used in place of the alkoxysilane when a proper liquidness can be attained and a solvent for the alkoxysilane is suitable for the alkoxytitanium. The alkoxytitanium includes tetra-i-propyl titanate, tetra-n-butyl titanate, tetrastearyl titanate, triethanolamine titanate, titanium acetylacetonate, titanium ethylacetoacetate, titanium lactate, tetraoctylene glycol titanate, etc. There may also be used oligomers produced by the polymerization of several molecules of any of these compounds.

(3) Coating Materials Containing a Water-Soluble Polymer and a Crosslinking Agent Therefor A coating material for forming a hydrophilic surface can be obtained by mixing as a crosslinking agent the alkoxysilane or alkoxytitanium exemplified in the above item (2) with the water-soluble polymer exemplified in the above item (1). In this case, although water may be used as a solvent, an alcohol solvent such as methanol, ethanol or the like is preferably used because a plate for the cell repels the coating material when it has a high water-repellency.

(4) Simultaneous Use of an Alkoxysilane Solution and an Alkali Solution

When a solution of the alkoxysilane exemplified in the above item (2) is applied on the plate and then heated at approximately 120 to 180° C. for several minutes, a coating film of silicon oxide is formed on the plate surface. Then, the dip of the plate in an alkaline solution enhances the hydrophilicity of the surface. Finally, the impartment of hydrophilicity is completed by washing away the alkaline solution with water. As the alkaline solution, there is preferably used an aqueous solution of a hydroxide such as sodium hydroxide, potassium hydroxide or the like, or a solution of the hydroxide in an alcohol or an aqueous alcohol. The dip time can be reduced with an increase of the concentration of the solution, though it is varied depending on the kind of the hydroxide used. For example, when sodium hydroxide is used, the dip time is preferably 1 to 5 minutes at a concentration of the solution of 1% by weight and is preferably approximately 10 to 30 seconds at a concentration of the solution of 5% by weight. As a solvent used in the alkoxysilane solution, alcohol solvents, ester solvents or ether solvents are suitable because employment of a ketone solvent (e.g., acetone and methyl ethyl ketone) tends to cause the conversion of the alkoxysilane to silicon oxide. In particular, the alcohol solvents are especially suitable because when the plate is a resin, they hardly dissolve the resin.

[5] Water-Repellent Material and a Treating Method

There is suitably used a conventional water-repellent material containing elements such as fluorine and silicon in the molecule. Such a material is dissolved in a solvent and the resulting solution is applied on a plate for the cell. Then, the solvent is evaporated by drying the plate, to form a thin film of the water-repellent material. The water-repellent material is chemically bonded to the cell surface by heating after the application, depending on the kind of the water-repellent material. Such a material to be chemically bonded to the cell surface is more suitable because there is only slight fear that owing to repeated use of the cell, this water-repellent material may move gradually to the hydrophilic patterns to cause the disappearance of the patterns. As such a material, the following compounds can be exemplified. These compounds react with hydroxyl groups and the like in the cell surface to form chemical bonds on the surface. Therefore, they are unlikely to move on the cell surface and are not liable to cause the disappearance of the hydrophilic patterns.

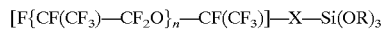

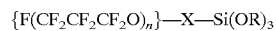

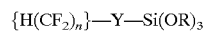

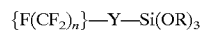

wherein X is a linking site between a perfluoro polyether chain and an alkoxysilane residue, Y is a linking site between a perfluoroalkyl chain and an alkoxysilane residue, and R is an alkyl group.

Specific examples of the material are the following compounds 1 to 12.

| | |
|---|---|
| $F\{CF(CF_3)-CF_2O\}_n-CF(CF_3)-CONH-(CH_2)_3-Si(OCH_2CH_3)_3$ | Compound 1 |
| $F\{CF(CF_3)-CF_2O\}_n-CF(CF_3)-CONH-(CH_2)_3-Si(OCH_3)_3$ | Compound 2 |
| $F(CF_2CF_2CF_2O)_n-CF_2CF_2-CONH-(CH_2)_3-Si(OCH_2CH_3)_3$ | Compound 3 |
| $F(CF_2CF_2CF_2O)_n-CF_2CF_2-CONH-(CH_2)_3-Si(OCH_3)_3$ | Compound 4 |
| $H(CF_2)_6-CONH-(CH_2)_3Si(OCH_2CH_3)_3$ | Compound 5 |
| $H(CF_2)_6-CONH-(CH_2)_3-Si(OCH_3)_3$ | Compound 6 |
| $H(CF_2)_8-CONH-(CH_2)_3-Si(OCH_2CH_3)_3$ | Compound 7 |
| $H(CF_2)_8-CONH-(CH_2)_3-Si(OCH_3)_3$ | Compound 8 |
| $F(CF_2)_6-CH_2CH_2-Si(OCH_3)_3$ | Compound 9 |
| $F(CF_2)_8-CH_2CH_2-Si(OCH_3)_3$ | Compound 10 |
| $F(CF_2)_6-CH_2CH_2-Si(OCH_2CH_3)_3$ | Compound 11 |
| $F(CF_2)_8-CH_2CH_2-Si(OCH_2CH_3)_3$ | Compound 12 |

Of these, compounds 1 to 8 are obtained by practicing the following synthesis processes. Compounds 9 to 12 are commercially available as 1H,1H,2H,2H-perfluorooctyltrimethoxysilane, 1H,1H,2H,2H-perfluorooctyltriethoxysilane, 1H,1H,2H,2H-perfluorodecyltrimethoxysilane and 1H,1H,2H,2H-perfluorodecyltriethoxysilane, respectively, from HYDRUS Chemical Inc. As another commercially available material, there can be exemplified Oputu-ru DSX manufactured by DAIKIN Industries Co., Ltd.

(Synthesis of Compound 1)

Krytox 157FS-L (average molecular weight: 2,500) manufactured by E. I. du Pont de Nemours & Co. (25 parts by weight) is dissolved in PF-5080 manufactured by 3M Co., Ltd. (100 parts by weight), followed by adding thereto thionyl chloride (20 parts by weight), and the resulting mixture is refluxed with stirring for 48 hours. The thionyl chloride and the PF-5080 are evaporated with an evaporator to obtain chloro carbonate form of Krytox 157FS-L (25 parts by weight). PF-5080 (100 parts by weight), Saira ace S330 manufactured by Chisso Co., Ltd. (3 parts by weight) and triethylamine (3 parts by weight) are added to the chloro carbonate form, and the resulting mixture is stirred at room temperature for 20 hours. Then, the reaction mixture is filtered through Fine Flow A, a radiolyte manufactured by Showa Chemical Industry Co., Ltd., and the PF-5080 in the filtrate is evaporated with an evaporator to obtain compound 1 (20 parts by weight).

(Synthesis of Compound 2)

Compound 2 (20 parts by weight) is obtained in the same manner as in the synthesis of compound 1, except for using Saira ace S360 manufactured by Chisso Co., Ltd. (3 parts by weight) in place of Saira ace S330 manufactured by Chisso Co., Ltd. (3 parts by weight).

(Synthesis of Compound 3)

Compound 3 (30 parts by weight) is obtained in the same manner as in the synthesis of compound 1, except for using Demnum SH (average molecular weight: 3,500) manufactured by DAIKIN Industries Co., Ltd. (35 parts by weight) in place of Krytox 157FS-L (average molecular weight: 2,500) manufactured by E. I. du Pont de Nemours & Co. (25 parts by weight).

(Synthesis of Compound 4)

Compound 4 (30 parts by weight) is obtained in the same manner as in the synthesis of compound 1, except for using Saira ace S360 manufactured by Chisso Co., Ltd. (3 parts by weight) in place of Saira ace S330 manufactured by Chisso Co., Ltd. (3 parts by weight) and using Demnum SH (average molecular weight: 3,500) manufactured by DAIKIN Industries Co., Ltd. (35 parts by weight) in place of Krytox 157FS-L (average molecular weight: 2,500) manufactured by E. I. du Pont de Nemours & Co. (25 parts by weight).

(Synthesis of Compound 5)

Compound 5 (3.5 parts by weight) is obtained in the same manner as in the synthesis of compound 1, except for using 7H-dodecafluoroheptanoic acid (molecular weight: 346.06) manufactured by DAIKIN Industries Co., Ltd. (3.5 parts by weight) in place of Krytox 157FS-L (average molecular weight: 2,500) manufactured by E. I. du Pont de Nemours & Co. (25 parts by weight).

(Synthesis of Compound 6)

Compound 6 (3.5 parts by weight) is obtained in the same manner as in the synthesis of compound 1, except for using 7H-dodecafluoroheptanoic acid (molecular weight: 346.06) manufactured by DAIKIN Industries Co., Ltd. (3.5 parts by weight) in place of Krytox 157FS-L (average molecular weight: 2,500) manufactured by E. I. du Pont de Nemours & Co. (25 parts by weight) and using Saira ace S320 manufactured by Chisso Co., Ltd. (2 parts by weight) in place of Saira ace S330 manufactured by Chisso Co., Ltd. (2 parts by weight).

(Synthesis of Compound 7)

Compound 7 (4.5 parts by weight) is obtained in the same manner as in the synthesis of compound 1, except for using 9H-hexadecafluorononanoic acid (molecular weight: 446.07) manufactured by DAIKIN Industries Co., Ltd. (4.5 parts by weight) in place of Krytox 157FS-L (average molecular weight: 2,500) manufactured by E. I. du Pont de Nemours & Co. (25 parts by weight).

(Synthesis of Compound 8)

Compound 8 (4.5 parts by weight) is obtained in the same manner as in the synthesis of compound 1, except for using 9H-hexadecafluorononanoic acid (molecular weight: 446.07) manufactured by DAIKIN Industries Co., Ltd. (4.5 parts by weight) in place of Krytox 157FS-L (average molecular weight: 2,500) manufactured by E. I. du Pont de Nemours & Co. (25 parts by weight) and using Saira ace S320 manufactured by Chisso Co., Ltd. (2 parts by weight) in place of Saira ace S330 manufactured by Chisso Co., Ltd. (2 parts by weight).

Any of the compounds described above is dissolved in a fluorine-containing solvent and the resulting solution is applied on a plate for the cell. Then, the compound is reacted with hydroxyl groups, carboxyl groups and the like in the cell surface by heating the plate for the cell, to form chemical bonds. Thus, the impartment of water-repellency is completed. The concentration of the water-repellent material is set so as to be increased with an increase of the average molecular weight of the material. When the average molecular weight is about 3,000, the concentration is preferably about 0.3% by weight. Specific examples of the fluorine-containing solvent are FC-72, FC-77, PF-5060, PF-5080, HFE-7100 and HFE-7200 which are manufactured by 3M Co., Ltd., and Vertrel XF manufactured by E. I. du Pont de Nemours & Co. The heating temperature is preferably 100° C. or higher. When the heating temperature is 120° C. or higher, the reaction for forming a film can be allowed to proceed more rapidly. The heating time is preferably about 1 hour at 100° C., about 15 minutes at 120° C., or about 10 minutes at 140° C. However, when the heating temperature is 250° C. or higher, care should be taken because the water-repellent material tends to be pyrolyzed. When no hydroxyl group or the like is present in a plate for the cell, hydroxyl groups can be given to the surface of the plate by carrying out $O_2$ plasma treatment. When the impartment of water-repellency is carried out after the $O_2$ plasma treatment, it becomes possible to form chemical bonds between the aforesaid water-repellent material and the plate for the cell. The water-repellent material is formed into a film by a coating method such as brushing, dip coating, spin coating or the like.

[6] Analyzer (1) Measuring Mechanism

Figure 3:
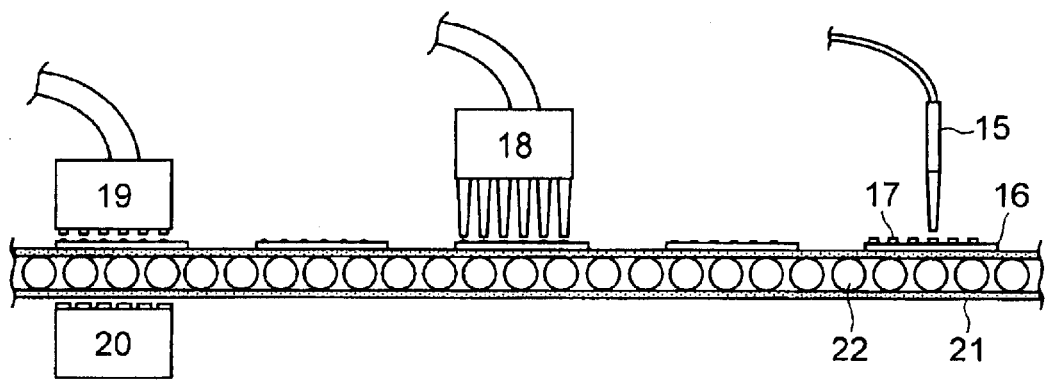
FIG. 3 illustrates the measuring mechanisms of the analyzer of the present invention.
Figure 3:
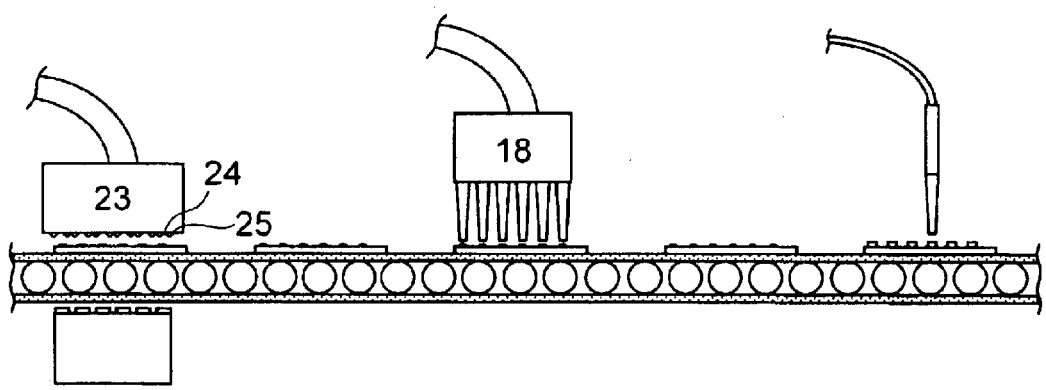

FIG. 3 shows the measuring mechanism of the analyzer of the present invention.

(A) When Transmittance or Reflectance is Measured

The following measuring mechanism is used when the flat cell transmits measuring light to a certain extent. A liquid sample 17 to be analyzed is delivered to a flat cell 16 from a dispenser 15 to adhere to the hydrophilic patterns on the surface of the flat cell. Then, indicators are delivered to the liquid sample on the surface of the flat cell from a dispenser for indicator delivery 18. After the sample reacts with the indicators, the transmittances or absorbances of the hydrophilic pattern portions are measured. The measurements are carried out by the use of measuring light emitted by a light exposure unit 19 which passes through the hydrophilic patterns of the flat cell and is then introduced into a light receptor 20. The analysis results are obtained by investigating and analyzing the percentage of a decrease in the measuring light at a specific wavelength which is caused by the passage through the flat cell. In order to improve the precision of measurement, it is preferable to measure previously the absorbance or transmittance of the hydrophilic patterns of the flat cell before adhering the sample or the like to the hydrophilic patterns.

The light exposure unit may have one light source for each hydrophilic pattern. However, when the light exposure unit becomes too large because of its two or more light sources, sending light to a plurality of light exposure units by branching a light source is advantageous in that the light exposure units can be miniaturized. In this case, optical fiber or the like is convenient for sending light to the light exposure units from the light source.

(B) When Reflectance is Measured

The following mechanism is used when the flat cell reflects measuring light to a certain extent. In the measurement, measuring light is emitted toward the hydrophilic patterns of the flat cell by the light exposure unit 24 of an optical system 23, and a portion of the measuring light is reflected by the flat cell. The residual light is absorbed by mixtures of a sample and an indicator on the hydrophilic patterns, the cell surface and the like. The reflected light is introduced into a receptor 25. The analysis results are obtained by carrying out the same investigation and analysis as in the above item (A). In order to improve the precision of measurement, it is preferable to measure previously the reflectance of the hydrophilic patterns of the flat cell before adhering the sample or the like to the hydrophilic patterns.

As to the light source of the light exposure unit, sending light to a plurality of exposure units by branching a light source is advantageous in that the light exposure units can be miniaturized, as in the above item (A) where the transmittance or reflectance is measured.

(2) Washing Mechanism for the Flat Cell

FIG. 4 shows a mechanism for washing the flat cell of the present invention.

A flat cell 26 subjected to the measurement is washed with water or washing water containing a surface-active agent, which is delivered from a washer 27. When the surface-active agent is used, it is removed by washing the flat cell 26 with water lastly, to re-improve the water-repellency of the cell surface.

A washed flat cell 28 is dried by a dryer 29. In order to conduct the drying rapidly, the dryer is preferably one which blows off hot air. A high wind velocity of the dryer is preferable because it facilitates the evaporation of water on the cell surface.

(3) Structure of the Analyzer

FIG. 5 shows the structure of the analyzer of the present invention.

When broadly sectioned, the analyzer shown in FIG. 5 comprises a measuring mechanism 30, a flat cell washing mechanism 31, a mechanism for conveyance of washed flat cell 32, a flat cell accommodating mechanism 33 and a mechanism for storage and supply of indicators 34. Feed openings for analyzing reagent 35 are present near the mechanism for storage and supply of analyzing reagents. A feed opening for liquid sample 36 is also present. In addition, the analyzer has a piping for water supply 37 and a piping for drainage 38, for washing of the flat cell. The analysis is controlled by a control unit 39 such as a computer. The analyzer and the control unit are connected to each other by a cable 40.

The flat cell washing mechanism can be placed in another housing in order to miniaturize the analyzer. The miniaturization makes it possible to locate the analyzer in a place where water-supply and drainage installations cannot be located.

EXAMPLES

The present invention is more concretely illustrated with the following examples, which should not be construed as limiting the scope of the invention.

Example 1

At first, a process for producing a flat cell is described below. A transparent polycarbonate plate (5 cm long, 11 cm wide and 0.5 mm thick) (mfd. by Fujimoto Chemicals Co., Ltd.) was irradiated with $O_2$ plasma. An apparatus used for the irradiation was a Plasma Asher Model IPC-8005T manufactured by Daionikusu Inc. The pressure inside the chamber before oxygen introduction was 0.1 Torr or less. The pressure inside the chamber after the oxygen introduction was 0.5 Torr. The output of the high-frequency power source of the apparatus was 100 W. The time of the plasma irradiation of the polycarbonate plate was 60 seconds. By the above treatment, the contact angle between the polycarbonate plate surface and water was reduced to 100 or less. The thus treated polycarbonate plate was attached to an OHP film (an OHP film TYPE PPC-DX A4, mfd. by RICOH Company Ltd.), and images were formed on the polycarbonate plate surface with an ink-jet printer. The ink-jet printer used was EM-900C manufactured by EPSON Inc. As the images, closed circles with a diameter of 3 mm were formed at 3-mm intervals so as to be arranged in six columns and in 10 rows, namely, 60 circles were formed. The number of a sample was also printed on the plate. Then, the polycarbonate plate was removed from the OHP film and dried at 50° C. for 5 minutes. The circles formed, i.e., the portions having ink adhered thereto served as masks in the subsequent step, i.e., the impartment of water-repellency.

Next, a 0.3 wt % solution of compound 1 was prepared. A solvent used in the solution was Flolinate PF-5080, a fluorine-containing solvent manufactured by 3M Co., Ltd. The above-mentioned polycarbonate plate was immersed in the solution for 60 seconds and then heated at 100° C. for 30 minutes. When the closed-circle printed portions of the polycarbonate plate were washed with water, the closed circles disappeared and washing water adhered to the portions where the closed circles had been present. The adhering water was evaporated by heating for 10 minutes in a chamber thermostated at 80° C. Thus, the desired flat cell was produced. FIG. 6 shows the flat cell produced.

In the manner described above, a water-repellent portion 41 and hydrophilic patterns 42 had been formed. The closed circles formed with the ink-jet printer had become the hydrophilic patterns owing to the removal of the ink. The corners of the plate had been cut (numerals 43 and 44 in FIG. 6) so that the analyzer could recognize the direction of the flat cell. Thus, mechanical measurement with such an analyzer does not cause confusion of measuring items and hence can be efficiently carried out. Needless to say, the number of corners cut off from the plate may be one, and it is not particularly limited so long as the direction of the flat cell can be recognized. The contact angle between the water-repellent portion and water was 115° and the contact angle between the hydrophilic pattern and water was 10° or less. Since each hydrophilic pattern corresponds to one conventional cell, each flat cell corresponds to 60 conventional cells.

A plurality of such flat cells were produced and then set in the analyzer shown in FIG. 5. FIG. 3, (1) shows the measuring mechanism of the analyzer. As the measuring mechanism, there was used a mechanism in which quantitation was carried out by measuring transmittance or absorbance. In the measurement, a liquid sample was adhered to hydrophilic patterns of the flat cell at first. To each hydrophilic pattern was adhered 0.5 $\mu$l of the liquid sample. Even when adhered in this volume, the liquid sample spread throughout the hydrophilic pattern and did not spread to the water-repellent portion. Since the maximum thickness of the sample in the pattern immediately after the adhesion of the liquid sample was about 0.1 mm, the liquid sample dried soon at ordinary temperature. To each hydrophilic portion was adhered 0.5 to 1 $\mu$l of a corresponding indicator. The indicator was adhered before drying of the liquid sample. The volume of the indicator adhered was that required for coloration of the sample to a degree necessary for the measurement. Next, the measurement was carried out by investigating the degree of attenuation of light incident on the flat cell. In the measurement, the accuracy of quantitatively determined values was enhanced by measuring the absorptance of the flat cell itself for measuring light too and taking the absorptance into consideration in the quantitative determination.

The flat cell after the measurement was washed by the washing mechanism shown in FIG. 4. Emission of a jet of warm water at 60° C. (3 ml/sec) for 1 second was carried out twice for each hydrophilic pattern. Thus, the sample and the reagents were removed. Then, the flat cell was dried in warm air to be regenerated. Warm water hardly adhered to the water-repellent portion. Even if warm water adhered to the water-repellent portion, it could easily be removed by exposure to warm air.

When a conventional rectangular parallelepipedic cell is used, filling the cell with a liquid sample becomes easier with a decrease of the surface tension of the liquid sample. In the case of a water-containing liquid sample (surface tension: 60 mN/m or more), the dimensions of the base of the cell should be at least 4 mm×4 mm. If the dimensions are less than 4 mm×4 mm, bubbles are formed on the wall surfaces of the cell when the cell is filled with the liquid sample. Moreover, since the level of the liquid sample introduced into the cell is at least 10 mm, the volume of the liquid sample should be at least 160 µl. This volume is approximately 100 to 160 times that required in the present example. In the case of a cell having a 4 mm×4 mm base, the liquid sample introduced into the cell will not come out even when the cell is turned upside down after measurement. This trouble is caused by the surface tension of the liquid sample, and the sample is not exhausted unless the sample is sucked or vibrated. In addition, since a conventional rectangular parallelepipedic cell has a shape more complicated than a planar shape, the volume of warm water required for washing the cell is larger than that required for washing the flat cell. In fact, when the conventional cell was washed by directing a jet of warm water (3 ml/sec) at the cell two or more times, the number of warm-water-jet directing operations required for regenerating the cell was 200. Since each flat cell of the present example permits the same measurement as that using 60 conventional cells, the number of flat cells to be washed was one-sixtieth that required in the case of conventional cells. Therefore, the volume of water necessary for the washing could be further reduced.

Thus, employment of the flat cell permits measurement using a smaller volume of a liquid sample as compared with a conventional cell. Moreover, a measuring apparatus using the flat cell permits reduction of the volume of water used for washing the cell as compared with a conventional rectangular parallelepipedic cell.

Comparative Example 1

A sheet (5 cm long and 11 cm wide) of black paper having 60 holes with a diameter of 3 mm on the surface (used as a mask against ultraviolet rays) was attached to a polystyrene plate (5 cm long, 11 cm wide and 0.5 mm thick). The polystyrene plate having the sheet attached thereto was irradiated with ultraviolet light for 2 minutes by the use of an ultraviolet irradiation apparatus (mfd. by Toshiba Raitex Corp.) equipped with a 800-W low-pressure mercury lamp to adjust the contact angle between the irradiated portion and water to 100 or less. The mask was peeled off, and a 1 wt % aqueous sodium alginate solution (viscosity: 300 cps) was applied on the ultraviolet-irradiated portions and then dried at ordinary temperature for 1 day. A sample and indicators were adhered to the ultraviolet-irradiated portions in the same manner as in Example 1, after which the thus treated plate was washed by the same method as in Example 1. However, the sodium alginate and the adsorbed sample and indicators could not be removed. The same results as above were obtained when a 1 wt % poly(vinylpyrrolidone) (average molecular weight: 40,000) aqueous solution was used in place of the 1 wt % aqueous sodium alginate solution (viscosity: 300 cps). The above results indicate that when a hydrophilic polymer is held on the sample-holding portions, the plate is difficult to wash.

Example 2

The production of flat cells and measurement were carried out in the same manner as in Example 1 except for adopting the dip method shown in FIG. 7, as a method for adhering a liquid sample to the flat cells, to obtain the same results as obtained in Example 1. This fact indicates that the sample can be subjected to measurement not only by its adhesion with a dispenser but also by the use of a vessel containing the liquid sample.

Although FIG. 7 shows an optical system for carrying out analysis by the measurement of absorbance or transmittance, there may also be used an optical system in which reflectance is measured. The measuring mechanism shown in FIG. 7 is as follows. A flat cell 45 is taken out of a flat cell cartridge 46 with tweezers 47 and immersed in a liquid sample in a vessel for liquid sample 48. The flat cell 45 is pulled out of the liquid sample to obtain flat cell 50 having the liquid sample adhered thereto. This cell is placed on a belt conveyor 51. Indicators are delivered to the cell from a dispenser for indicator delivery 52. Light emitted by a light exposure unit 53 reaches a light receptor 54 through hydrophilic patterns having the sample adhered thereto. Thus, measurement is carried out.

Example 3

The time of the $O_2$ plasma irradiation of the same polycarbonate plate as used in Example 1 for the flat cell production was varied, and the contact angle between the water-repellent portion and water and the contact angle between the hydrophilic pattern and water were measured. Table 1 shows the results obtained. In all the cases, the output of a high-frequency power source was 100 W.

TABLE 1

Time of $O_2$ plasma irradiation of the polycarbonate plate, the contact angle between the hydrophilic pattern and water, and the absorbance ratio in a portion having a sample adhered thereto

| Irradiation time (sec) | Contact angle between hydrophilic pattern and water (°) | B/A |
|---|---|---|
| 0 | 95 | 0.72 |
| 10 | 42 | 0.92 |
| 20 | 32 | 0.94 |
| 25 | 29 | ≧0.95 |
| 30 | 24 | ≧0.95 |
| 40 | 17 | ≧0.95 |
| 50 | 12 | ≧0.95 |
| 60 | ≦10 | ≧0.95 |
| 70 | ≦10 | ≧0.95 |
| 80 | ≦10 | ≧0.95 |

The contact angle of the hydrophilic pattern tends to be reduced with an increase of the irradiation time. That is, the hydrophilicity is enhanced with an increase of the irradiation time.

Next, the absorbance distribution in the hydrophilic pattern was investigated. FIG. 8 shows portions of measuring the transmittance distribution in the hydrophilic pattern. In this measurement, there was calculated the ratio of the transmittance of a portion 1 mm apart from the center of the hydrophilic pattern to that of the center. When a measuring beam is focused, namely, when measurement is carried out in a part of the hydrophilic pattern, the quantitativeness of the cell is decreased with an increase of the concentration distribution of a sample in the hydrophilic pattern. Therefore, the above-mentioned transmittance ratio should be close to 1.

Table 1 also shows values of B/A wherein A denotes the absorbance of the center and B denotes the absorbance of a portion 1 mm apart from the center. When the ratio B/A has a value considerably smaller than 1, the cause for this is as follows: a liquid sample becomes protuberant in the central portion of the pattern and dries as iChisso that the amount of the sample in the central portion becomes larger than that in the peripheral portion. If this phenomenon takes place, the quantitativeness in measurement is deteriorated when the diameter of the measuring beam is smaller than that of the hydrophilic pattern.

For adhering the liquid sample, there was used the mechanism used in Example 2, i.e., the mechanism comprising immersing a flat cell in a vessel containing the sample. The wavelength of measuring light was 450 nm. A measuring light spot was a circle with a diameter of 1 mm. The sample was a phenolphthalein solution (concentration; 0.002% by weight, solvent; water:ethanol=9:1). An indicator was a sodium acetate solution (solvent; water:ethanol=1:1).

From Table 1, the following can be seen. When the contact angle between the hydrophilic pattern and water was less than 30, the B/A ratio had a value of 0.95 or more, namely, the quantitativeness was satisfactory. However, when the contact angle was more than 30°, the B/A ratio had a value of less than 0.95, namely, the quantitativeness was deteriorated.

The above results indicate that in the flat cell, the contact angle between the hydrophilic pattern and water is preferably less than 30° in order to improve the precision of analysis. Moreover, they indicate that also in the analyzer, the contact angle between water and the hydrophilic pattern of the flat cell used for improving the precision of analysis is preferably less than 30°.

Example 4

Flat cells were produced in the same manner as in Example 1 except for changing the concentration of the compound 1 solution to 0.03% by weight and varying the dip time. Table 2 shows the dip time and the contact angle between the water-repellent portion and water.

TABLE 2

Time of dip of the polycarbonate plate in the compound 1 solution, the contact angle of the water-repellent portion, and the adhesion of a liquid sample to the water-repellent portion

| Immersion time (sec) | Contact angle between water-repellent portion and water (°) | Adhesion of liquid specimen |
| --- | --- | --- |
| 1 | 96 | X |
| 3 | 98 | X |
| 5 | 100 | ○ |
| 10 | 105 | ○ |
| 30 | 111 | ○ |
| 60 | 113 | ○ |
| 90 | 115 | ○ |
| 120 | 115 | ○ |
| 180 | 116 | ○ |

*:
○; No liquid specimen adhered to the water-repellent portion.
X; A liquid specimen adhered to the water-repellent portion.

Then, a liquid sample was adhered to the flat cells in the same vessel for liquid sample as used in Example 2, to find that in some of the flat cells, the liquid sample adhered also to the portion other than the hydrophilic patterns. Table 2 also shows this result.

This result suggests that when the contact angle between the water-repellent portion and water is less than 100°, the sample adheres to the portion other than the hydrophilic patterns, so that a bridge-like droplet is formed among two or more of the patterns. Particularly when measurement is carried out for a plurality of different items, the droplet tends to cause a problem of erroneous measurement due to mixing of the sample and indicators.

Thus, it was revealed that a contact angle between the water-repellent portion and water of 100° or more is advantageous.

Example 5

The same procedure as in Example 1 was carried out except for using a 0.3 wt % solution of compound 2 in PF-5080 in place of the 0.3 wt % solution of compound 1 in PF-5080, to produce the same flat cells as produced in Example 1. The contact angle between the water-repellent portion and water was 115° which was the same as in the case of using compound 1. An analyzer using the aforesaid flat cells permitted analysis using small amounts of a sample and reagents, as in Example 1. The cells after the analysis could be regenerated by washing and drying.

Example 6

The same procedure as in Example 1 was carried out except for using a 0.3 wt % solution of compound 3 in PF-5080 in place of the 0.3 wt % solution of compound 1 in PF-5080, to produce the same flat cells as produced in Example 1. The contact angle between the water-repellent portion and water was 117°. An analyzer using the aforesaid flat cells permitted analysis using small amounts of a sample and reagents, as in Example 1. The cells after the analysis could be regenerated by washing and drying.

Example 7

The same procedure as in Example 1 was carried out except for using a 0.3 wt % solution of compound 4 in PF-5080 in place of the 0.3 wt % solution of compound 1 in PF-5080, to produce the same flat cells as produced in Example 1. The contact angle between the water-repellent portion and water was 117°. An analyzer using the aforesaid flat cells permitted analysis using small amounts of a sample and reagents, as in Example 1. The cells after the analysis could be regenerated by washing and drying.

Example 8

The same procedure as in Example 1 was carried out except for using a 0.3 wt % solution of compound 5 in PF-5080 in place of the 0.3 wt % solution of compound 1 in PF-5080, to produce the same flat cells as produced in Example 1. The contact angle between the water-repellent portion and water was 110°. An analyzer using the aforesaid flat cells permitted analysis using small amounts of a sample and reagents, as in Example 1. The cells after the analysis could be regenerated by washing and drying.

Example 9

The same procedure as in Example 1 was carried out except for using a 0.3 wt % solution of compound 6 in PF-5080 in place of the 0.3 wt % solution of compound 1 in PF-5080, to produce the same flat cells as produced in Example 1. The contact angle between the water-repellent portion and water was 110°. An analyzer using the aforesaid flat cells permitted analysis using small amounts of a sample and reagents, as in Example 1. The cells after the analysis could be regenerated by washing and drying.

Example 10

The same procedure as in Example 1 was carried out except for using a 0.3 wt % solution of compound 7 in PF-5080 in place of the 0.3 wt % solution of compound 1 in PF-5080, to produce the same flat cells as produced in Example 1. The contact angle between the water-repellent portion and water was 111°. An analyzer using the aforesaid flat cells permitted analysis using small amounts of a sample and reagents, as in Example 1. The cells after the analysis could be regenerated by washing and drying.

Example 11

The same procedure as in Example 1 was carried out except for using a 0.3 wt % solution of compound 8 in PF-5080 in place of the 0.3 wt % solution of compound 1 in PF-5080, to produce the same flat cells as produced in Example 1. The contact angle between the water-repellent portion and water was 110°. An analyzer using the aforesaid flat cells permitted analysis using small amounts of a sample and reagents, as in Example 1. The cells after the analysis could be regenerated by washing and drying.

Example 12

The same procedure as in Example 1 was carried out except for using a 0.3 wt % solution of compound 9 in PF-5080 in place of the 0.3 wt % solution of compound 1 in PF-5080, to produce the same flat cells as produced in Example 1. The contact angle between the water-repellent portion and water was 112°. An analyzer using the aforesaid flat cells permitted analysis using small amounts of a sample and reagents, as in Example 1. The cells after the analysis could be regenerated by washing and drying.

Example 13

The same procedure as in Example 1 was carried out except for using a 0.3 wt % solution of compound 10 in PF-5080 in place of the 0.3 wt % solution of compound 1 in PF-5080, to produce the same flat cells as produced in Example 1. The contact angle between the water-repellent portion and water was 114°. An analyzer using the aforesaid flat cells permitted analysis using small amounts of a sample and reagents, as in Example 1. The cells after the analysis could be regenerated by washing and drying.

Example 14

The same procedure as in Example 1 was carried out except for using a 0.3 wt % solution of compound 11 in PF-5080 in place of the 0.3 wt % solution of compound 1 in PF-5080, to produce the same flat cells as produced in Example 1. The contact angle between the water-repellent portion and water was 112°. An analyzer using the aforesaid flat cells permitted analysis using small amounts of a sample and reagents, as in Example 1. The cells after the analysis could be regenerated by washing and drying.

Example 15

The same procedure as in Example 1 was carried out except for using a 0.3 wt % solution of compound 12 in PF-5080 in place of the 0.3 wt % solution of compound 1 in PF-5080, to produce the same flat cells as produced in Example 1. The contact angle between the water-repellent portion and water was 114°. An analyzer using the aforesaid flat cells permitted analysis using small amounts of a sample and reagents, as in Example 1. The cells after the analysis could be regenerated by washing and drying.

Example 4 reveals that with an increase of the contact angle between the water-repellent portion of the flat cell and water, the hydrophilic pattern can be made smaller, so that the amount of a sample can be reduced. From Examples 1 and 5 to 15, it was found that in the present invention, the contact angle between the water-repellent portion of the flat cell and water can be adjusted to 110° or more by properly using any of the following compounds:

$$[F\{CF(CF_3)-CF_2O\}_n-CF(CF_3)]-X-Si(OR)_3$$

$$\{F(CF_2CF_2CF_2O)_n\}-X-Si(OR)_3$$

$$\{H(CF_2)_n\}-Y-Si(OR)_3$$

$$\{F(CF_2)_n\}-Y-Si(OR)_3$$

wherein X is a linking site between a perfluoro polyether chain and an alkoxysilane residue, Y is a linking site between a perfluoroalkyl chain and an alkoxysilane residue, and R is an alkyl group.

Example 16

The same procedure as in Example 1 was carried out except for using a transparent polyether sulfone plate of 0.5 mm thickness in place of the polycarbonate plate of 0.5 mm thickness, to produce flat cells having the same performance characteristics as attained in Example 1. An analyzer using these flat cells permitted the same analysis as carried out in Example 1. Thus, it was revealed that the flat cells can be produced by using a plate other than polycarbonate so long as the plate is transparent.

Example 17

A flat cell was produced by carrying out the same procedure as in Example 1 except for using a planished SUS304 plate of 0.08 mm thickness in place of the polycarbonate plate of 0.5 mm thickness and changing the O₂ plasma irradiation time to 180 seconds from 60 seconds. Unlike the cell in Example 1, the thus produced cell was used not for measuring reflectance or absorbance but for measuring reflectance.

A plurality of such flat cells were produced and then set in the analyzer shown in FIG. 5. As the measuring mechanism of the analyzer, there was used the mechanism shown in FIG. 3, (2) in which quantitation was carried out by measurement of reflectance. Except for using this mechanism, the same measurement as in Example 1 was carried out.

As a result, it was found that as in Example 1, analysis could be carried out by the use of the flat cells by measuring reflectance in place of transmittance or absorbance. The analyzer having the measuring mechanism for measuring reflectance in place of transmittance or absorbance permitted analysis using small amounts of a sample and reagents, as in Example 1. The cells after the analysis could be regenerated by washing and drying.

Thus, it was revealed that analysis can be carried out by adopting a method for measuring reflectance in place of transmittance or absorbance, so long as a plate for the flat cell reflects measuring light even though it is not transparent.

Example 18

Flat cells having the same performance characteristics as attained in Example 17 were produced by carrying out the same procedure as in Example 17 except for using a planished Fe-42Ni plate of 0.08 mm thickness in place of the SUS304 plate of 0.08 mm thickness. When the same analyzer as in Example 17 was used, the cells permitted analysis using small amounts of a sample and reagents, as in Example 17. The cells after the analysis could be regenerated by washing and drying.

Thus, it was revealed that analysis can be carried out by adopting a method for measuring reflectance in place of transmittance or absorbance, so long as a plate for the flat cell reflects measuring light even though it is not SUS304.

The present invention has made it possible to provide a cell that singly permits a plurality of measurements for the same sample, can be reused after washing and drying, and can easily be washed because of its simple planar structure. Furthermore, the present invention has made it possible to provide an analyzer using said cell.

It should be further understood by those skilled in the art that the foregoing description has been made on embodiments of the invention and that various changes and modifications may be made in the invention without departing from the spirit of the invention and scope of the appended claims.

What is claimed is:

1. A measurement cell for analyzer for carrying out qualitative and/or quantitative analysis for one or more substances by an optical means, wherein a sample to be subjected to measurement is liquid, said measurement cell has a substantially planar shape, said measurement cell has sample-holding portions in said plane, the sample-holding portions provide a contact angle of 30° or less with water, a portion other than said sample-holding portions provides a contact angle of 100° or more and 117° or less with water, and said measurement cell can be repeatedly used by washing and drying.

2. The measurement cell for analyzer according to claim 1, wherein a layer of a compound having any of the following structures is formed on the portion other than the sample-holding portions:

$$[F\{CF(CF_3)-CF_2O\}_n-CF(CF_3)]-X-Si(OR)_3$$

$$\{F(CF_2CF_2CF_2O)_n\}-X-Si(OR)_3$$

$$\{H(CF_2)_n\}-Y-Si(OR)_3$$

$$\{F(CF_2)_n\}-Y-Si(OR)_3$$

wherein X is a linking site between a perfluoropolyether chain and an alkoxysilane group, Y is a linking site between a perfluoroalkyl chain and an alkoxysilane group, n is between 6 and 21, and R is an alkyl group.

3. The cell according to claim 1, which has a transmissivity of 60% or more for light having a wavelength of 340 to 800 nm.

4. The cell according to claim 1, which has a transmissivity of 80% or more for light having a wavelength of 400 to 800 nm.

5. The cell according to claim 1, wherein a plate for said cell is a metal that reflects light.

6. The cell according to claim 1, wherein said cell has a surface roughness of sample sticking area of Ra 100 nm or less.

* * * * *